(12) United States Patent
Christensen et al.

(10) Patent No.: US 8,269,193 B2
(45) Date of Patent: Sep. 18, 2012

(54) HANDHELD FLUOROMETER AND METHOD OF USE

(75) Inventors: William M. Christensen, Hibbing, MN (US); Eugene Tokhtuev, Duluth, MN (US); Brian Philip Carlson, Lakeville, MN (US); Paul R. Kraus, Apple Valley, MN (US); Benedict F. Pesigan, Apple Valley, MN (US); Jill Marie Klegin, Cannon Falls, MN (US); Adrian Eugene Hartz, Woodbury, MN (US); Michael Patrick Kremer, Rosemount, MN (US)

(73) Assignee: Ecolab USA Inc., St. Paul, MN (US)

( * ) Notice: Subject to any disclaimer, the term of this patent is extended or adjusted under 35 U.S.C. 154(b) by 116 days.

(21) Appl. No.: 12/750,822

(22) Filed: Mar. 31, 2010

(65) Prior Publication Data

US 2011/0240887 A1  Oct. 6, 2011

(51) Int. Cl.
*G01N 21/64* (2006.01)
(52) U.S. Cl. .................................. 250/461.1; 250/461.2
(58) Field of Classification Search ................. 50/461.1, 50/461.2
See application file for complete search history.

(56) References Cited

U.S. PATENT DOCUMENTS

| 4,178,512 | A | * | 12/1979 | Frungel et al. ............. 250/461.1 |
| 4,783,314 | A | | 11/1988 | Hoots et al. |
| 4,808,849 | A | * | 2/1989 | Inculet et al. ................. 307/400 |
| 6,255,118 | B1 | | 7/2001 | Alfano et al. |
| 6,369,894 | B1 | | 4/2002 | Rasimas et al. |
| 6,831,745 | B2 | | 12/2004 | Marquardt et al. |
| 6,842,243 | B2 | | 1/2005 | Tokhtuev et al. |
| 6,977,729 | B2 | | 12/2005 | Marquardt et al. |
| 7,095,500 | B2 | | 8/2006 | Banks |
| 7,154,603 | B2 | | 12/2006 | Banks |
| 7,179,384 | B2 | | 2/2007 | Moriarty et al. |
| 7,198,755 | B2 | | 4/2007 | Tokhtuev et al. |
| 7,220,382 | B2 | | 5/2007 | Godfrey et al. |
| 7,550,746 | B2 | | 6/2009 | Tokhtuev et al. |
| 2003/0058450 | A1 | * | 3/2003 | Mosley et al. ................. 356/436 |
| 2003/0160182 | A1 | * | 8/2003 | Petrich et al. .............. 250/458.1 |

(Continued)

FOREIGN PATENT DOCUMENTS

WO   2007143047 A1   12/2007

OTHER PUBLICATIONS www.psi.cz (Manual for Aqua Pen P AP-P100) (available in 2010).*

(Continued)

*Primary Examiner* — Christine Sung
(74) *Attorney, Agent, or Firm* — Fredrikson & Byron, PA

(57) ABSTRACT

Embodiments provide a handheld fluorometer and method of determining a concentration of a product within a sample. In some cases the handheld fluorometer includes an immersible sensor head that measures a fluorescence of the product and a controller that calculates the concentration of product. In some cases the handheld fluorometer includes a handheld controller module, an immersible sensor head connected to the controller module, a sample cup for containing a water sample, and a fastener that removably fastens the sample cup about the immersible sensor head. In some cases the sensor head is angled with respect to the controller module and the fluorometer provides a substantially stable base. The sample cup can be removed to acquire a sample of water containing the product and then refastened about the sensor head for determining the concentration.

24 Claims, 12 Drawing Sheets

U.S. PATENT DOCUMENTS

| | | | |
|---|---|---|---|
| 2005/0229698 A1 | 10/2005 | Beecroft et al. | |
| 2006/0246595 A1 | 11/2006 | Banks et al. | |
| 2008/0030712 A1* | 2/2008 | Tokhtuev et al. | 356/51 |
| 2008/0240997 A1* | 10/2008 | Kaiga et al. | 422/82.08 |
| 2009/0212236 A1 | 8/2009 | Tokhtuev et al. | |
| 2009/0283698 A1 | 11/2009 | Chapman | |

OTHER PUBLICATIONS

Turner Designs, Aquafluor Handheld Fluorometer and Turbidimeter User's Manual, Sep. 2004, Version 1.3, pp. 1-36.

Turner BioSystems, Picofluor Handheld Flurorometer Operating Manual, Feb. 2010, Version 1.5, pp. 1-16.

Nalco, Traced Antiscalant Control with RO-TRASAR, copyright 2003-2009, accessed on Apr. 9, 2010 from http://www.extranet.nalco.com/ASP/applications/membrane_tech/equipment/ro_trasar.asp, pp. 1-2.

International Search Report and Written Opinion for PCT/IB2011/051304, Jan. 10, 2012, 8 pages.

* cited by examiner

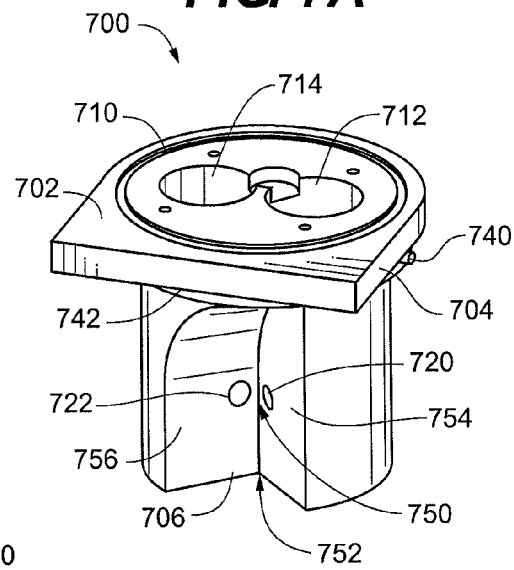
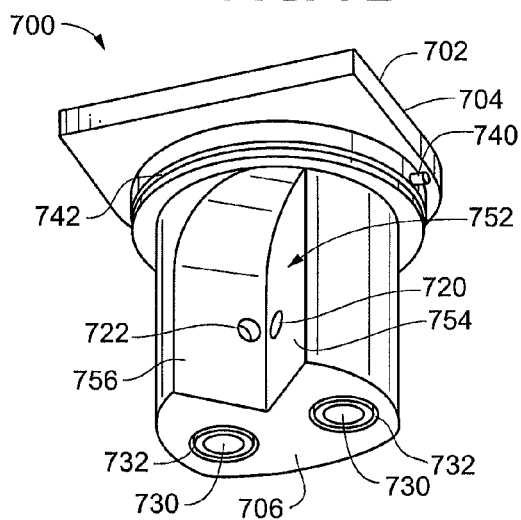
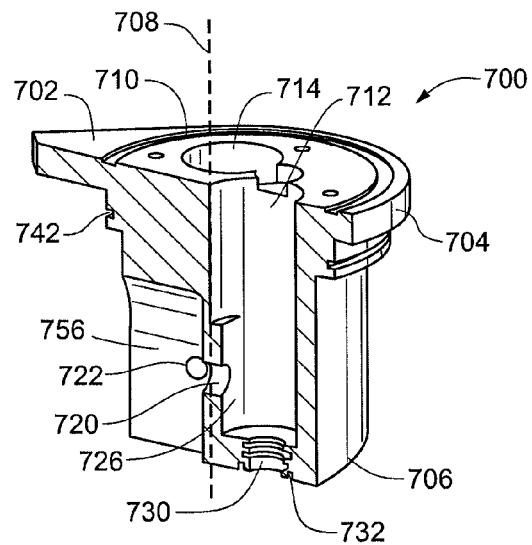

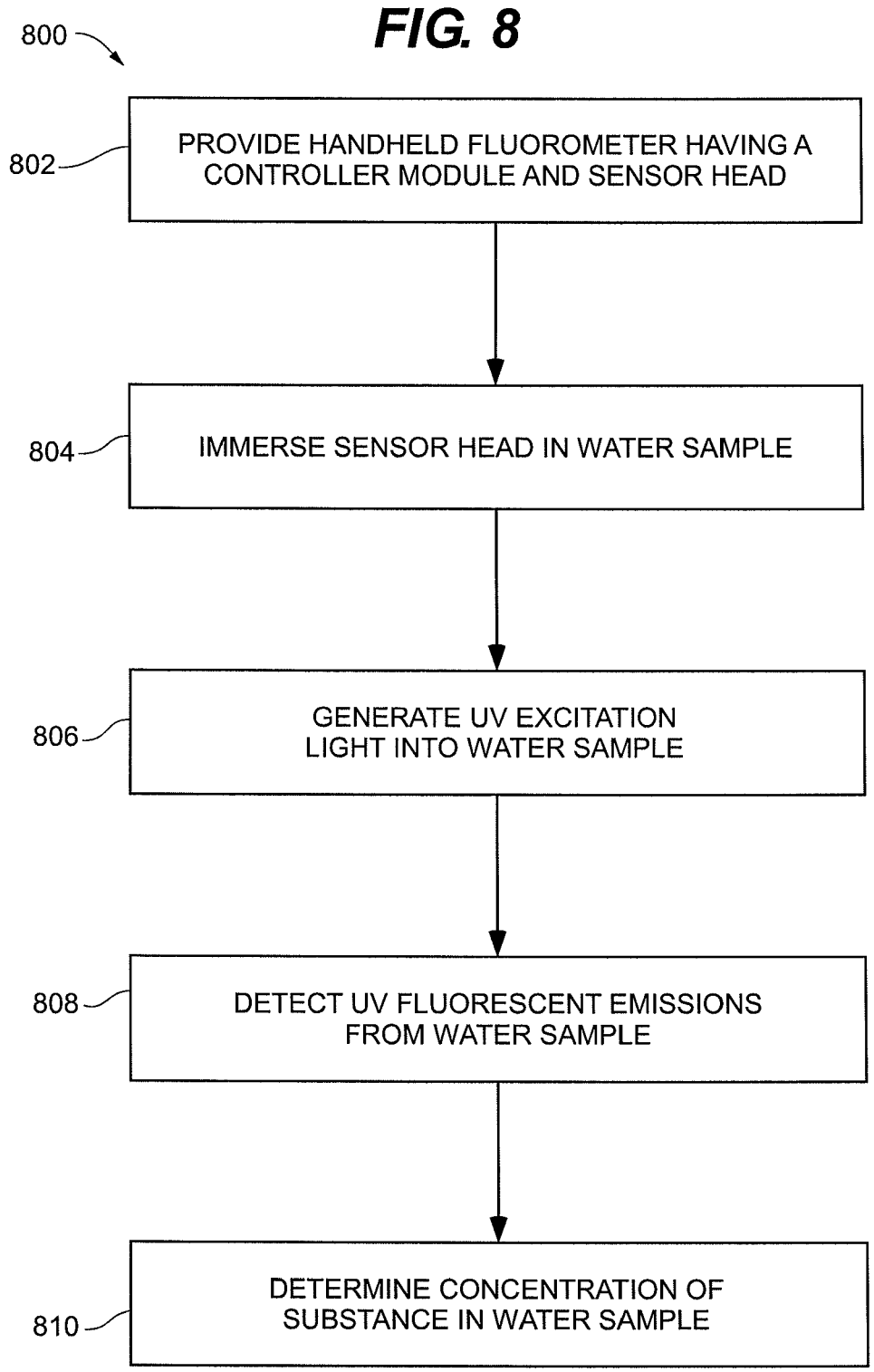

HANDHELD FLUOROMETER AND METHOD OF USE

BACKGROUND

Embodiments of the present invention generally relate to optical measuring devices for testing a liquid sample, and more particularly to fluorometric sensors and fluorometers for determining and monitoring the concentration of one or more substances in a liquid sample.

In cleaning and antimicrobial operations, commercial users (e.g., restaurants, hotels, food and beverage plants, grocery stores, etc.) rely upon the concentration of the cleaning or antimicrobial product to make the product work effectively. Failure of a cleaning or antimicrobial product to work effectively (due to concentration issues) can cause a commercial user to perceive the product as lower quality. End consumers may also perceive the commercial user as providing inferior services. In addition, commercial users may be investigated and/or sanctioned by government regulatory and health agencies. Accordingly, there is a need for a system that can determine if the concentration of a product is within a specified concentration range. The same may be true for other applications, such as water care, pest control, beverage and bottling operations, packaging operations, and the like.

One method of monitoring the concentration of a product relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence.

Fluorometric spectroscopy concerns the detection of fluorescent light emitted by a sample of interest. It involves using a beam of light, usually ultraviolet (UV) light, that excites the electrons in molecules of certain compounds in the sample and causes them to emit light of a lower energy (i.e., to "fluoresce"). There are several types of fluorometers for measuring emitted fluorescence. Fluorometers generally have of a source of excitation radiant energy, an excitation wavelength selector, a sample cell to contain the sample material, an emission wavelength selector, a detector with signal processor and a readout device. Filter fluorometers use optical filters to isolate the incident light and fluorescent light. Spectrofluorometers use diffraction grating monochromators to isolate the incident light and fluorescent light.

SUMMARY

Embodiments of the invention generally relate to various designs for a handheld fluorometer having an immersible sensor head capable of emitting excitation light into a sample of interest and then detecting and measuring fluorescent emissions from the sample. Embodiments of the handheld fluorometer are advantageously self-contained and incorporate components that allow the handheld fluorometer to generate the excitation light, detect and measure fluorescent emissions from the sample, calculate a concentration of one or more substances in the sample, and display the determined concentration(s) to a user, without the need for communication with exterior equipment.

According to one aspect of the invention, a handheld fluorometer is provided having a handheld controller module, an immersible sensor head connected to the controller module, a sample cup for containing a water sample, and a fastener that removably fastens the sample cup about the sensor head. The controller module includes an elongated housing having a bottom surface. The controller module also includes a controller that determines a concentration of a substance in the water sample based on a detected fluorescent emission, a display coupled to the controller for displaying the concentration, and an input interface that allows a user to enter data for use by the controller. The immersible sensor head includes a light source and an emission detector coupled to the controller and a housing having a proximal end, a distal end, and a longitudinal axis. The sensor head is connected to the bottom surface of the controller module at the proximal end of the sensor head housing. The sensor head housing also includes a light source window that transmits excitation light from the light source to an analytical area outside the sensor head housing, and an emission detector window that transmits fluorescent emissions from the analytical area to the emission detector. The fastener removably fastens the sample cup about the sensor head such that at least the light source window and the emission detector window can be immersed in the water sample contained in the sample cup and the water sample can occupy the analytical area outside the sensor head housing.

According to another aspect of the invention, a handheld fluorometer is provided that includes a handheld controller module and an immersible sensor head connected to the handheld fluorometer. The handheld controller module has an elongated housing with a bottom surface and a first end and a second end between which extends a longitudinal axis of the housing. The controller module also has a controller that determines a concentration of a substance in a water sample based on a detected fluorescent emission. The controller module also includes, among other things, a display coupled to the controller for displaying the concentration. The immersible sensor head comprises, among other things, a UV light source and a UV emission detector coupled to the controller. The sensor head also includes a housing having a proximal end and a distal end between which extends a longitudinal axis of the sensor head. The sensor head is connected to the bottom surface of the controller module housing at the proximal end of the sensor head housing such that the longitudinal axis of the sensor head is approximately perpendicular to the longitudinal axis of the controller module housing. The sensor head also includes a light source window that transmits UV excitation light from the UV light source inside the sensor head housing to an analytical area outside the sensor head housing, and an emission detector window that transmits UV fluorescent emissions from the analytical area to the UV emission detector inside the sensor head housing.

According to another aspect of the invention, a method is provided for measuring fluorescent emissions from a substance and determining the concentration of the substance within a water sample. The method includes providing a handheld fluorometer having a handheld controller module and an immersible sensor head connected to a bottom surface of the controller module at a proximal end of the sensor head. The method also includes immersing the sensor head in a water sample containing a concentration of a substance, and then generating and directing UV excitation light into the water sample, which causes the substance to fluoresce. The method also includes detecting UV fluorescent emissions from the water sample with the handheld fluorometer and determining the concentration of the substance in the water sample with the handheld fluorometer based on the detected UV fluorescent emissions.

Embodiments of the present invention can provide one or more of the following features and/or advantages.

Some embodiments provide an improved UV handheld fluorometer with improved sensitivity by, e.g., incorporating an efficient micro optics configuration to measure fluorescent signals at an angle (e.g., 90 degrees) to the direction of the excitation beam. Some embodiments provide a useful handheld fluorometer that combines a handheld controller handle with an immersion (dip) probe connected to (e.g., fixedly attached or integral with) the controller handle. Accordingly, in some cases the UV handheld fluorometer can be used as a dip probe to measure fluorescent emissions in open water. In some cases the handheld fluorometer can be used under typical field conditions to measure water samples in a sample cup. When used in a laboratory environment, some embodiments of the handheld fluorometer can measure fluorescent emissions in an included sample cup or in a glass beaker or other container. In some cases the handheld fluorometer can be secured with a holding member and inserted into a flow cell to provide continuous measurements and concentrations from a single sample or a number of samples varying with time. Accordingly, the portable and handheld nature of the handheld fluorometer in some embodiments provides flexibility with regard to the placement of the fluorometer's sensor head. As just a few examples, the fluorometer can be used easily and conveniently within a warewashing machine, sink, mop bucket, laundry machine and the like.

Some embodiments provide improved performance in measuring fluorescence from a fluorescent tracer such as naphthalene disulfonate (NDSA). In some cases a polyester film filter having a thickness of about 0.5+/−0.2 mm is positioned between an emission filter and the photodetector within a handheld fluorometer. Incorporating such a polyester film can in some cases minimize stray light levels to allow measurements of NDSA fluorescence in samples with a turbidity as high as 100 Nephelometric Turbidity Units (NTU).

Some embodiments provide improved accuracy by providing a UV handheld fluorometer with means for making temperature measurements and compensating for temperature, in some cases based on the specific fluorescent marker being assessed. Further, some embodiments provide for convenient field measurements using a UV handheld fluorometer including a novel sampling cup which can be secured on the body of the UV handheld fluorometer. In some cases the sample cup serves as a reservoir for the water sample and also supports a desired position of the fluorometer when it is placed on a flat support surface.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 7A is a top perspective view of a sensor head according to some embodiments of the invention.

FIG. 7B is a bottom perspective view of the sensor head of FIG. 7A.

FIG. 7C is a perspective, cross-sectional view of the sensor head of FIG. 7A.

FIG. 8 is a flow diagram depicting a method for determining a concentration of a substance in a water sample according to some embodiments of the invention.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention generally provide a handheld optical measuring device having an immersible sensor head and methods of using such a device. Components of the handheld optical measuring device are advantageously self-contained in a handheld configuration, providing a convenient tool for a variety of uses. In some embodiments of the invention, an optical measuring device in the form of a handheld fluorometer is provided. While some embodiments of the invention are described herein with reference to a handheld fluorometer, it should be understood that aspects of the invention can be embodied in a variety of optical measuring devices (e.g., turbidimeter, optical absorbance meter, etc.) and the invention is not limited to any particular form of device.

Figure 1:
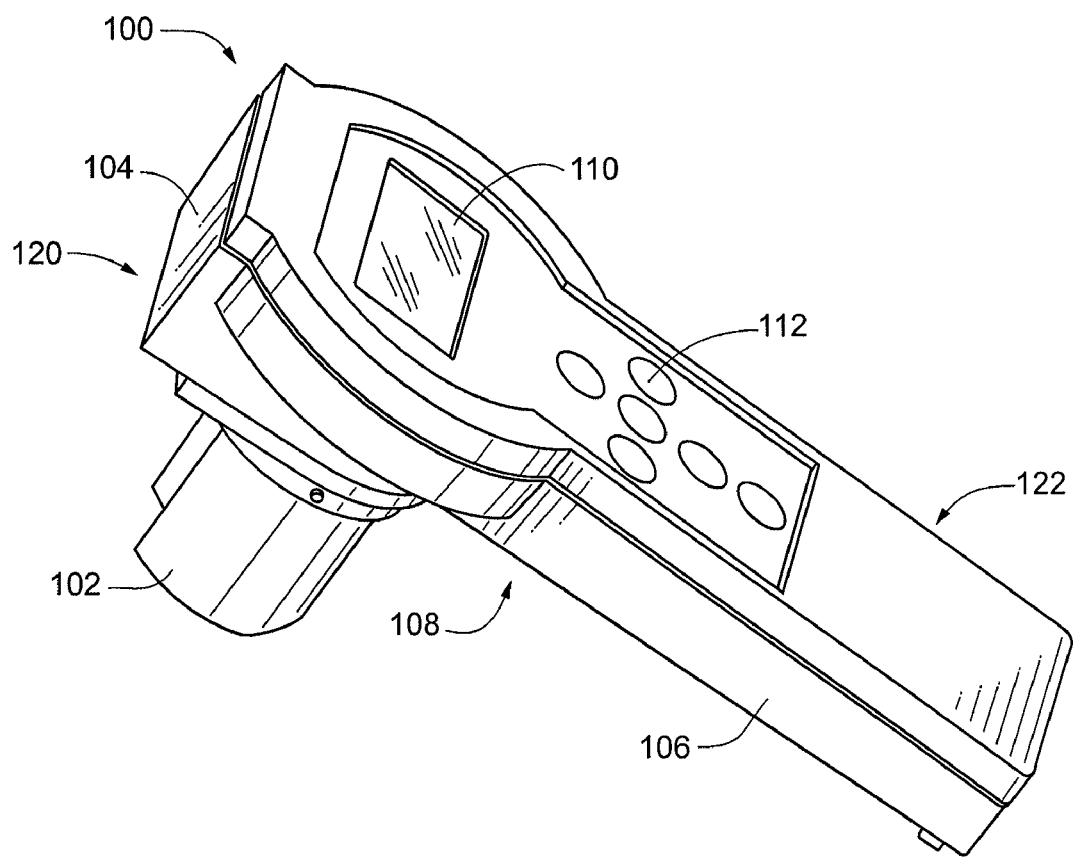
FIG. 1 is a perspective view of a handheld fluorometer according to some embodiments of the invention.

FIG. 1 is a perspective view of an optical measuring device in the form of a handheld fluorometer 100 according to some embodiments of the invention. The fluorometer 100 generally includes an immersible sensor head 102 connected to a handheld controller module 104. The controller module 104 also includes an electronic display 110 for displaying sensor readings and calculations to a user, and an input interface in the form of a keypad 112 that allows the user to interact with the fluorometer 100 (e.g., entering variables, setting parameters, accessing menu items, etc.).

According to some embodiments, the controller module 104 has a generally elongated housing 106 which provides a convenient form, similar to a handle or wand, to easily grasp or hold the fluorometer 100 by the hand. The sensor head 102 preferably includes a water-tight housing that enables it to take measurements and otherwise function when partially or wholly immersed in a liquid sample of interest. Accordingly, in some cases the sensor head 102 has some features and/or characteristics similar to an immersible dip probe. For example, in some embodiments of the invention the immersible sensor head 102 has one or more features and/or components similar to those described in commonly-assigned U.S. Pat. No. 7,550,746 and U.S. Patent Application Publication 2009/0212236, the entire contents of each of which is hereby incorporated herein by reference. The configuration of the immersible sensor head 102 can also be contrasted in some ways with fluorometers and other optical instruments that position sensors and other components exterior to an optical cell containing the sample of interest.

In some cases the sensor head 102 is connected to (e.g., attached to or integral with) a bottom surface 108 of the controller housing 106 opposite from the display 110 and positioned proximate a distal end 120 of the controller housing. In a typical fashion, a user can grasp the controller housing 106 near a proximal end 122 of the controller housing to take measurements from a sample, read the display 110, and/or manipulate the keypad 112. For example, a user may dip the sensor head 102 into a sample by holding the controller module 104 above the surface of a liquid sample (e.g., in a reservoir/container in the field, a beaker in the laboratory, etc.) with the sensor head 102 partially or completely immersed in the sample. In some embodiments, a user may grasp the second end of the controller module 104 while securing a sample cup filled with a sample about the immersible sensor head 102. Of course other configurations of the controller module and the sensor head are possible and the invention is not limited to any particular physical configuration.

In general, the handheld fluorometer 100 at minimum measures fluorescent emissions from a sample including a substance of interest (e.g., a chemical solution, such as an antimicrobial or cleaning product), calculates a concentration of the substance in the sample, and displays the determined concentration to a user. The user can then optionally perform any desired actions based on the determined concentration, such as, for example, adding more of the substance to an industrial system in order to increase the concentration of the substance. In this way, the fluorometer can be part of a manual feedback loop. If the fluorometer determines that the concentration is lower or higher than a threshold concentration, a user will see the difference and can adjust the product dispensation appropriately by either dispensing more or less product. Additionally, the fluorometer can function as part of an out-of-product alarm. When a product runs out, the fluorescence (which reflects the concentration of the product) will drop below a pre-determined threshold level. At this point, the sensor can alert a user that the dispenser is out of product. The signal can be a visual or audio signal, or a vibrating signal. Accordingly, such feedback will ensure that enough cleaner, antimicrobial or other composition is present to achieve the desired effect (cleanliness, reduction in microorganisms, lubrication, etc.).

The basic operation of fluorometers is well known, and accordingly, various details are omitted here for conciseness and clarity. In general, the fluorometer 100 calculates a concentration of a particular substance in a liquid sample based on fluorescent properties of the substance. As will be described in more detail herein, the fluorometer 100 includes a light source that emits light within a selected wavelength range. When the sensor head 102 is immersed in the liquid sample, the light encounters particles of the substance of interest, which excites the electrons in certain molecules of the substance and causes them to emit light of a lower energy (i.e., to "fluoresce") in another wavelength range. The sensor head 102 includes an optical sensor, such as a photodetector, that detects the fluorescent emissions and generates a corresponding electrical signal indicating the intensity of the fluorescent emissions. The fluorometer 100 includes a controller, coupled with the optical sensor, that can then calculate the concentration of the substance based on a known relationship between the intensity of the fluorescent emissions and the concentration of the substance.

A number of variations and specific details of this general process are contemplated for embodiments of the invention involving fluorometers. For example, the substance of interest may be any desired chemical solution having fluorescent properties. Examples include, but are not limited to, biocides such as pesticide and antimicrobial products, anticorrosion, antiscaling, and antifouling products, disinfectants, and other cleaning products, detergents, additives, and the like. For convenience, these and other such substances are alternately referred to herein simply as "products," "chemical solutions," "treatment solutions" and the like. In addition, although examples are presented herein involving determining the concentration of water treatment product(s) or solution(s) within a sample of cooling water (e.g., a water sample) used in various industrial systems (e.g., a cooling tower), it should be appreciated that the handheld fluorometer 100 may be useful in determining the concentration(s) of products used in numerous settings to treat water and other liquids. As just a few examples, the handheld fluorometer 100 may be useful for determining concentrations of one or more substances in laundry, automatic ware-washing, manual ware-washing, $3^{rd}$ sink applications, power sink applications, vehicle care, clean-in-place operations, healthcare applications, hard surface applications and the like.

Many products fluoresce in the presence of light radiating from the sensor head 102 because many of the compounds that make up the products have fluorescent characteristics. For example, a compound or molecule that has a benzene component can incorporate one or more substituent electron donating groups such as —OH, —$NH_2$, and —$OCH_3$, and polycyclic compounds that exhibit fluorescent characteristics. Many compounds used in the above-described applications include chemical structures like these, such as surfactants, lubricants, antimicrobial agents, solvents, hydrotropes, antiredeposition agents, dyes, corrosion inhibitors and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like. Examples of some of these compounds and corresponding applications can be found in U.S. Pat. No. 7,550,746, the entire content of which is herein incorporated by reference.

Additionally, or alternatively, fluorescent tracers (also referred to herein as "fluorescent markers") can be incorporated into products that may or may not already include naturally fluorescing compounds. Some non-limiting examples of tracers include naphthalene disulfonate (NDSA), 2-naphthalenesulfonic acid, Acid Yellow 7, 1,3,6,8-pyrenetetrasulfonic acid sodium salt, and fluorescein. In some embodiments the fluorescent tracer is added to the product in a known proportion, thus making it possible to estimate the concentration of the product once the concentration of the tracer is determined. For example, in some cases the concentration of the fluorescent tracer can be determined by comparing a current fluorescent signal with fluorescent signals from known tracer concentrations measured during a calibration procedure. The concentration of chemical product can then be estimated from the known nominal proportion of fluorescent tracer and measured concentration of fluorescent tracer. In some cases a current concentration of a product, $C_c$, in a liquid sample can be determined by $$C_c = C_m \times (C_0/C_f), \text{ wherein}$$

$$C_m = K_m \times (S_x - Z_0), \text{ and}$$

wherein $C_m$ is a current fluorescent marker concentration, $K_m$ is a slope correction coefficient, $S_x$ is a current fluorescent measurement, $Z_0$ is a zero shift, $C_0$ is a nominal concentration of the product, and $C_f$ is a nominal concentration of the fluorescent tracer.

Figure 2:
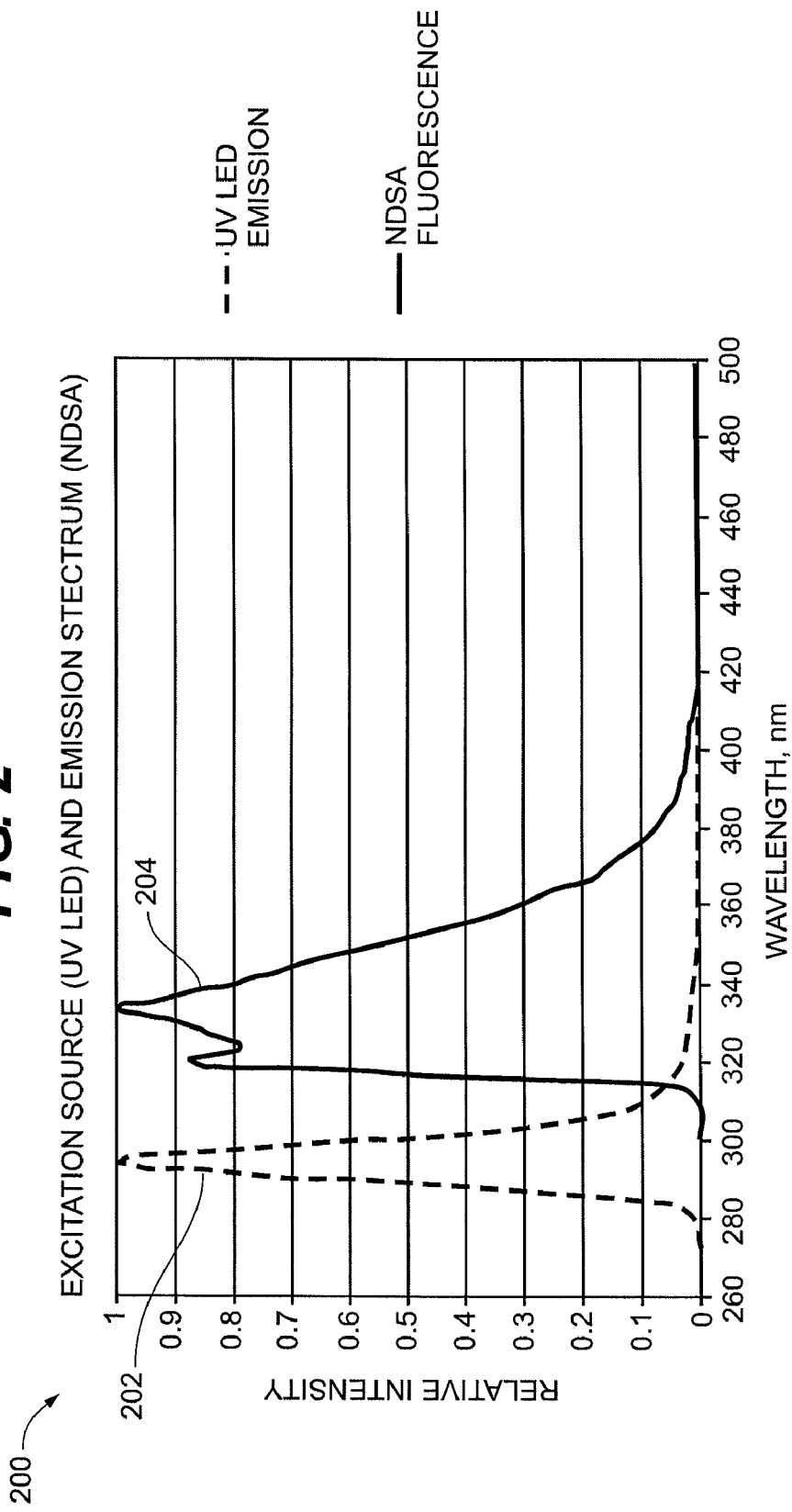
FIG. 2 is a plot of excitation and emission spectrum intensity according to some embodiments of the invention.

Referring to FIG. 2, a plot 200 is shown of an excitation spectrum intensity 202 and an emission spectrum intensity 204 according to some embodiments of the invention. In this example, a fluorometer having a light source in the form of an ultra violet (UV) light emitting diode (LED) emits excitation light within a range from about 280 nm to about 310 nm into a sample of cooling tower water having a product with an added fluorescent tracer, NDSA. The added NDSA absorbs this UV radiation and produces fluorescence in a range from about 310 nm to about 400 nm. The emission detector of the fluorometer detects this emitted radiation, and the fluorometer determines the concentration of the NDSA tracer, and ultimately the concentration of the product within the sample of the cooling tower water.

Figure 3:
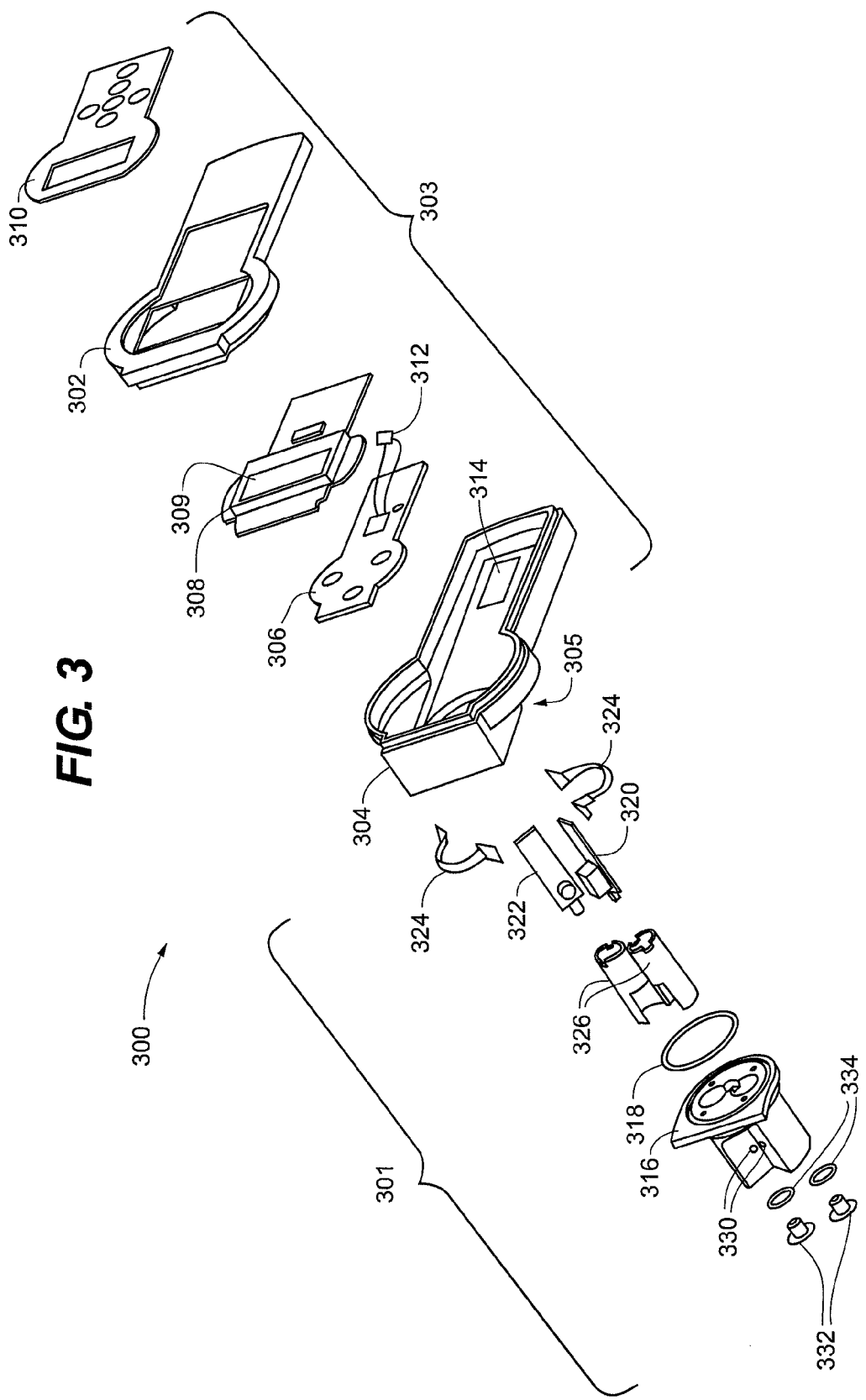
FIG. 3 is an exploded view of a handheld fluorometer according to some embodiments of the invention.

FIG. 3 is an exploded view of a handheld fluorometer 300 similar to the handheld fluorometer shown in FIG. 1. The fluorometer 300 generally includes an immersible sensor head 301 connected to a controller module portion 303. The controller module 303 includes a housing and several components within the housing. The housing is formed from a top portion 302 and a bottom portion 304, with the bottom portion 304 of the controller housing defining a bottom surface 305 on the exterior of the bottom portion. The sensor head 301 includes a sensor head housing 316 that is configured to be fixedly attached to the bottom surface 305 of the controller housing. In some embodiments the sensor head housing 316 may be integrally formed with one or more portions of the controller housing.

In some embodiments the controller module 303 generally includes those components necessary to determine a concentration of a product based on a signal received from the sensor head 301. As shown in FIG. 3, the controller module 303 includes a control board 306 that couples with a display board 308 via a display board cable 312. The display board 308 includes an electronic display 309 (e.g., an LCD screen) that displays information to a user. The controller module 303 also includes an input interface in the form of a membrane keypad overlay 310, which allows the user to enter a variety of information for use by the controller module 303. The controller module 303 also includes a portable power source, e.g., battery, 314 for powering the circuits within the fluorometer 300.

In some embodiments the immersible sensor head 301 has one or more features and/or components similar to those described in commonly-assigned U.S. Pat. No. 7,550,746 and U.S. Patent Application Publication 2009/0212236, the entire contents of each of which is hereby incorporated herein by reference. Referring back to FIG. 3, in some embodiments, the sensor head 301 includes a housing 316 that houses a light source board 320 and an emission detector board 322. A first O-ring 318 provides a seal between the sensor head housing 316 and the bottom portion 304 of the controller housing. The components on the light source board 320 and the emission detector board 322 are shielded by a brass tube 326 that substantially encircle each board. Each tube 326 includes a cutout at the distal end of the tube, and the sensor head housing 316 includes windows 330 extending through the housing. These cutouts and the windows 330 allow a light source (e.g., LED) positioned on the light source board 320 and an emission detector (e.g., photodetector) positioned on the emission detector board 322 to communication with an analytical area outside the sensor head housing 316. Electrical cables 324 couple the light source board 320 and the emission detector board 322 to the control board 306, which allows the controller on the board 306 to control the light source and receive signals back from the emission detector. In some embodiments the sensor head 301 also includes one or more temperature sensors that are able to measure the temperature of a water sample. For example, the light source board 320 and/or the emission detector board 322 may include one or more temperature sensors that extend into the sensor head housing 316. Covers 332 positioned in a distal face of the sensor housing 316, along with additional O-rings 334, provide a seal around the temperature sensors.

Figure 4:
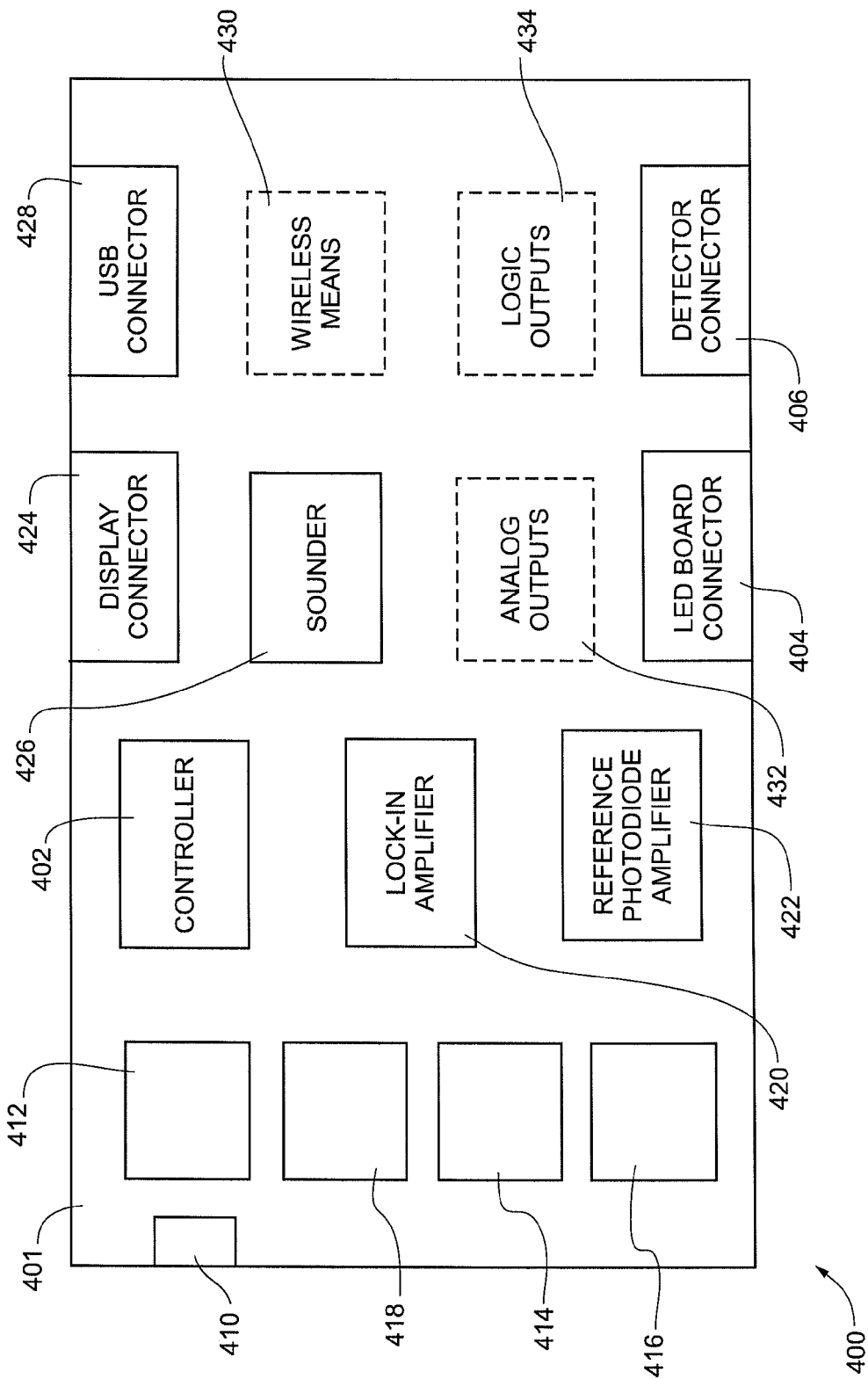
FIG. 4 is a schematic diagram of a controller board according to some embodiments of the invention.

FIG. 4 is a schematic diagram of a controller board 400 for a handheld fluorometer according to some embodiments of the invention. The controller board 400 can comprise a number of discrete components positioned (e.g., soldered) and coupled together (connections not shown) on a printed circuit board 401. FIG. 4 presents a simplified schematic of the basic components of one exemplary control board 400, and it will be appreciated by those skilled in the art that various connections between the components and/or details about components may vary. The control board 400 includes a controller 402, which calculates a concentration of a product within a water sample based on an intensity signal from the emission detector. The controller 402 may provide a variety of other functions, including without limitation, performing a calibration routine, accepting and executing instructions entered at the input interface, and/or formatting data for viewing on the fluorometer's display. The controller 402 can be embodied in any suitable form, such as a software driven microprocessor, a microcontroller, or a field programmable gate array, or a fixed hardware design such as an application specific integrated circuit, etc. In addition, the controller 402 may have onboard memory, or the control board may have memory (not shown) that stores instructions for execution by the controller 402.

The control board also includes a power cable with a connector 410 for connecting the board 400 to a power source such as the battery 314 shown in FIG. 3. The board 400 also includes a controller power supply 412, an analog power supply 414, and a light source power supply 416 for powering the light source in the sensor head. In some embodiments the control board 400 includes a real-time clock battery 418, a lock-in amplifier 420, a reference photodiode amplifier 422, and connectors for the display board 424, the light source board 404, and the emission detector board 406. In some cases, the control board 400 may also have a sounder 426, a USB or other type of data connector 428, wireless means 430 for communicating with other computing devices, and optional analog 432 and logical 434 outputs.

Figure 5:
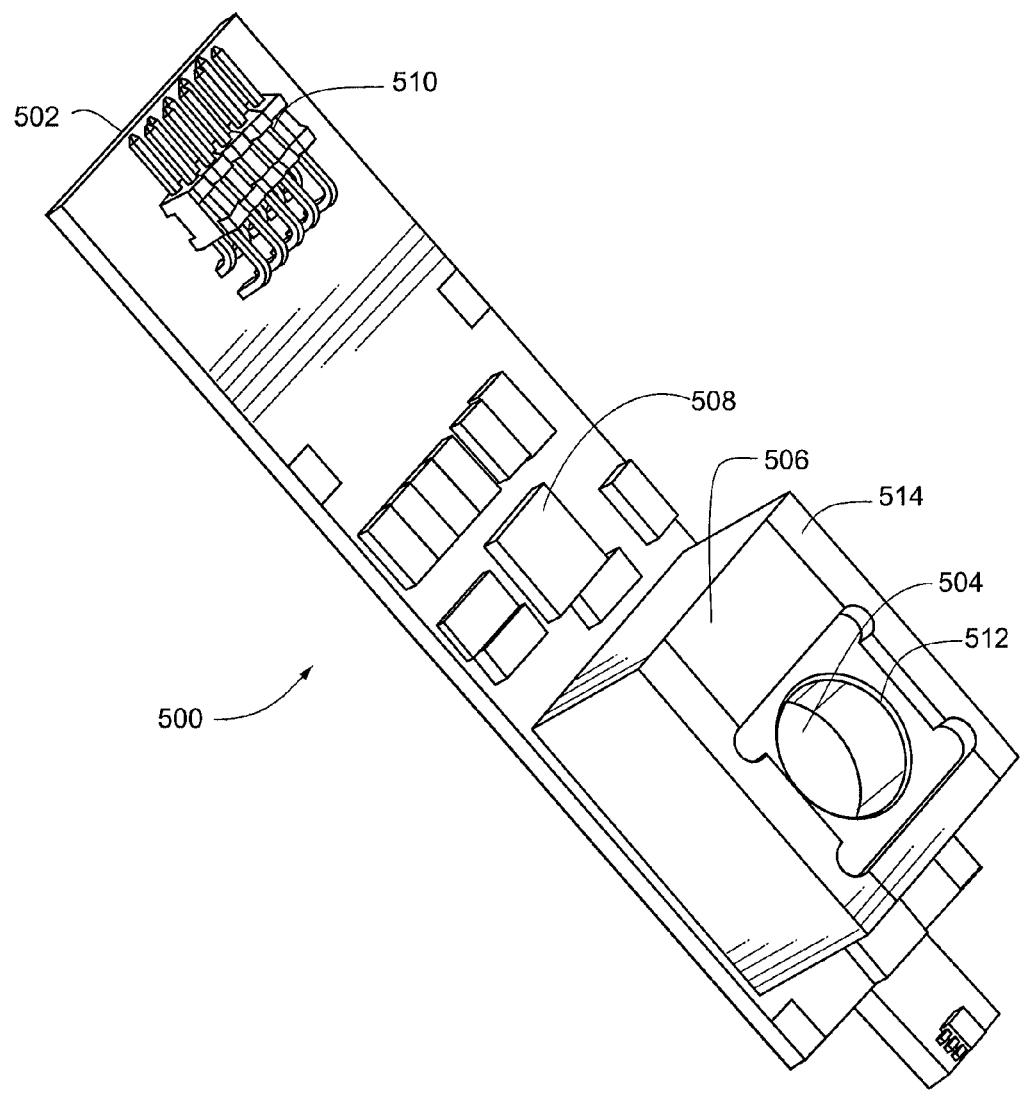
FIG. 5 is a perspective view of a light source board according to some embodiments of the invention.

FIG. 5 is a perspective view of a light source board 500 according to some embodiments of the invention. The board 500 (also shown in FIG. 3 as 320) generally includes a printed circuit board 502 having a light source 504 and a reference photodiode 506, along with a preamplifier 508 and a connector 510 for coupling the board 500 with the control board. An excitation filter 512 is positioned by a filter holder 514 over the light source 504, to filter the light from the light source 504 before it leaves the immersible sensor head. The light source 504 can include a variety of possible elements. For example, light source 504 may be a gas discharge lamp, a mercury lamp, a deuterium lamp, a metal vapor lamp, a light emitting diode (LED) or a plurality of LEDS. In addition, the light source 504 may emit excitation radiation in a number of possible spectrums depending upon the element chosen and the spectrum desired. In some embodiments the light source is an ultraviolet LED, capable of emitting light having a wavelength from about 280 nm to about 310 nm.

Figure 6:
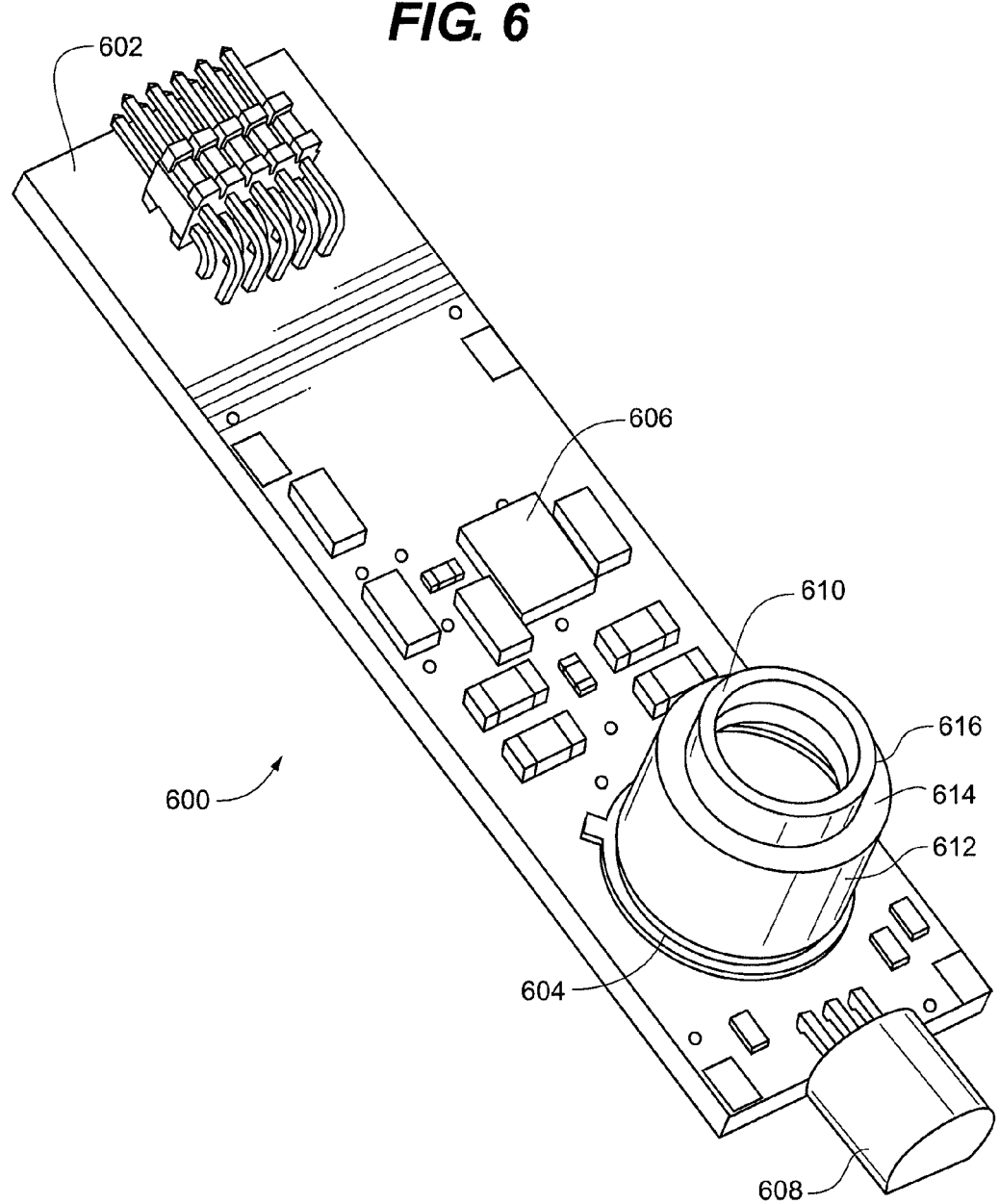
FIG. 6 is a perspective view of an emission detector board according to some embodiments of the invention.

FIG. 6 is a perspective view of an emission detector board 600 according to some embodiments of the invention. The detector board 600 generally includes a number of components, including an emission detector 604 positioned on a printed circuit board 602. In some embodiments of the invention, the emission detector 604 comprises a UV-sensitive photodiode. For example, the detector 604 may generate an intensity signal based on light from about 310 nm to about 400 nm that it detects from an analytical area outside the sensor head. The detector board 600 also includes a preamplifier 606 and a temperature sensor 608. An emission filter holder 610 positioned about the emission detector 604 supports one or more filters for screening the radiant energy and passing on the desired wavelengths to the detector 604. In the embodiment shown in FIG. 6, the filters include an interference filter 612 and a UG-11 glass filter 614. In some embodiments, an additional polyester film filter 616 is also positioned in front of the emission detector 604. In some cases the polyester film filter 616 has a thickness of about 0.5+/−0.2 mm. In some cases optical designs can provide increased optical efficiency (e.g., using ball lenses, highly divergent beams, etc.) but may also compromise the performance of interference filters which have a high efficiency and a high rejection value for collimated beams. Incorporating such a polyester film can in some cases minimize stray light levels to allow measurements of NDSA fluorescence in samples with a turbidity as high as 100 Nephelometric Turbidity Units (NTU).

FIGS. 7A-7C present various views of a discrete immersible sensor head 700 according to some embodiments of the invention that can be attached to a controller module of a handheld fluorometer such as of those previously discussed. FIG. 7A is a top perspective view of the sensor head 700, FIG. 7B is a bottom perspective view of the sensor head 700, and FIG. 7C is a perspective, cross-sectional view of the sensor head 700. The sensor head 700 can be made from a plastic and may be molded and/or milled to achieve the desired shape and features.

In general, the sensor head 700 comprises a housing 702 that includes a first vertical cavity or chamber 712 that is configured to receive a light source circuit board (e.g., the light source board 320 of FIG. 3 or 500 of FIG. 5). In some cases the light source chamber 712 is formed with a cylindrical configuration, which can provide a snug fit for the cylindrical brass shields 326 illustrated in FIG. 3. In some embodiments the light source chamber 712 has a partially-cylindrical configuration including a planar wall 726 along one lateral side of the chamber 712. Returning to FIGS. 7A-7C, the sensor head housing 702 includes a second vertical cavity or chamber 714 for receiving an emission detector circuit board (e.g., the emission detector board 322 of FIG. 3 or 600 of FIG. 6), similar to the light source chamber 712. In some cases the light source chamber 712 and the emission detector chamber 714 may be formed and positioned symmetrically about a longitudinal axis 708 of the sensor head 700, although this is not required in all embodiments.

The sensor head housing 702 further includes an angular cutout 752 in the exterior surface of the housing 702. In some embodiments the angle of the cutout 752 is approximately 90 degrees, although it should be understood that the invention is not limited to a particular angle for the cutout. The cutout 752 is bounded by a first wall 754 intersecting a second wall 756 at the longitudinal axis of the sensor head 700. The first wall 754 defines a light source window 720 that provides a path through the first wall 754 for excitation energy emitted by the light source. The second wall 756 similarly defines a emission detector window 722 that provides a path through the second wall 756 for fluorescent emissions to reach the emission detector located within the sensor head housing 702. In some embodiments, the light source window 720 and/or the emission detector window 722 comprise a channel extending through the sensor head housing 702. In some embodiments the windows 720, 722 also include a lens, prism or other material optically transparent to the light source radiation and/or fluorescent emissions. For example, in some embodiments a glass or sapphire ball lens is positioned within each channel. Other suitable materials known in the art may also be used. The ball lens provides the light source/detector window, but also provides a focusing means for directing light between the light source/detector and an analytical area 750 outside the housing 702 of the sensor head 700.

As shown in the figures herein, the angular cutout 752, including the light source window 720 and the emission detector window 722, are oriented with respect to the controller module such that the angular cutout and the windows face toward the distal end of the controller module. As discussed further herein, the angular cutout and the windows may be oriented in a different direction in some embodiments. For example, in some embodiments the angular cutout and the windows face toward the proximal end of the controller module.

In some embodiments, the sensor head 700 includes a proximal end 704 and a distal end 706, between which extends the longitudinal axis 708 and a length of the sensor head 700. As shown in FIGS. 1 and 3, in some embodiments the sensor head 700 is connected to the bottom surface of the controller module housing at or near the proximal end 704 of the sensor head 700. In some cases the sensor head 700 may be fixedly attached to the controller housing with a fastener. The fastener can include, but is not limited to, screws, bolts, and/or pins, or an adhesive or weld (not shown in the figures). In some embodiments the sensor head 700 is secured with four screws that compress an O-ring positioned in a groove 710 between the sensor head 700 and the controller module. In some embodiments, the sensor head housing 702 may be integrally formed with the controller module such that there is a seamless transition between the proximal end 704 of the sensor head and the bottom surface of the controller module.

In some embodiments the sensor head 700 also includes part or all of a fastener that removably fastens a sample cup about the sensor head 700. As just one example, the fastener may comprise one or more pins 740 positioned about the sensor head housing 702 and corresponding slots on the sample cup. In some embodiments the pins 740 and the slots form a bayonet fastener that secures the sample cup about the sensor head and also aligns the sample cup in a preferred orientation (e.g., rotation) about the sensor head 700. Other fasteners (e.g., screw threads, opposing pressure elements, etc.) can also be included.

In some embodiments the sensor head 700 also includes holes 730 for inserting one or more temperature sensor covers, such as those depicted in FIG. 3. Returning to FIGS. 7A-7C, the holes 730 may be threaded or otherwise configured to receive and secure the temperature sensor covers. The temperature sensors (not shown in FIGS. 7A-7C) are adapted to sense the current temperature of the water sample and generate a corresponding signal that can be used to correct concentration calculations based on errors due to, e.g., temperatures outside an acceptable range.

In addition, the sensor head 700 is preferably an immersible sensor head, meaning that it is partly or wholly immersed below the surface of a water sample when taking fluorescent emission measurements. Accordingly, the sensor head housing 702, connection to the controller housing, and any windows or other potential voids in the housing 702 are effectively sealed prior to immersion. For example, in some cases the housing 702 includes a first O-ring groove 710 at the proximal end 704 of the sensor head and second O-ring grooves 732 around the temperature sensor holes 730. In some embodiments including a sample cup, a third O-ring groove 742 may also be formed around the circumference of the sensor head 700 near the proximal end 704 of the sensor head in order to provide a substantially impermeable seal between the sample cup and the sensor head 700. In addition, the light source window 720 and emission detector window 722 may also be sealed with O-rings and the like. In some embodiments, the light source window 720 and emission detector window 722 are sealed due to a pressure fit between the window channels and the ball lenses placed within the channels.

FIG. 8 is a flow diagram depicting a method of determining a concentration of a product in a water sample according to some embodiments of the invention. In general, the fluorometer measures a fluorescent light emission of the active molecule in the product that is proportional to the actual concentration of the product in the water sample. After providing a handheld fluorometer having a controller module and a sensor head connected to the controller module (802), a water sample containing the product of interest is provided. The sensor head is immersed in the water sample (804) and the water sample occupies an analytical area of the sensor. Next, an ultraviolet (UV) excitation light having a first UV wavelength is generated by a light source in the sensor head and directed into the water sample and the analytical area (806). The sensor head then detects and measures the fluorescent emissions of the sample at a second UV wavelength (808). The sensor head includes a controller (402 in FIG. 4, for example) that calculates the concentration of the product in the sample based on the measured fluorescent emissions (810). The first wavelength may be in the range of 280-310 nm. The second UV wavelength may be in the range of 310 nm to 400 nm. The sensor may also measure a reference fluorescence emission of the sample at the first wavelength. The sensor may also measure a fluorescence emission of a zero solution having zero concentration of the chemical. In that case, the concentration of the chemical in the sample may be calculated based on the calculated difference in the measured fluorescent emission of the sample containing the chemical and the measured fluorescent emission of the zero solution. The concentration of the sample may also be calculated based on a calibration constant determined for known concentrations of the product in a calibration sample.

As an example, in some cases sample concentrations may be evaluated based upon signals from two UV detectors. A reference detector measures an intensity of the UV excitation generated by the light source, while a fluorescent emission detector measures an intensity of the fluorescent emissions emitted by the product. The calculation uses the following equations:

$$C_C = K_X \left( \frac{I_E^S}{I_R^S} - \frac{I_E^0}{I_R^0} \right)$$

where $C_C$ is an actual, current concentration of a product X (for example, a surfactant, an antimicrobial agent, etc) in a sample solution;

$K_X$ is a calibration coefficient;

$I_E^S$ is an output signal from the emission detector for the sample solution;

$I_R^S$ is an output signal from the reference detector for the sample solution;

$I_E^0$ is an output signal from the emission detector for a zero solution (i.e., a solution with zero concentration of the product); and $I_R^0$ is an output signal from the reference detector for the zero solution.

$$K_X = C_{CALIBR} \bigg/ \left( \frac{I_E^{CALIBR}}{I_R^{CALIBR}} - \frac{I_E^0}{I_R^0} \right)$$

where $C_{CALIBR}$ is a concentration of the product in a calibration solution;

$I_E^{CALIBR}$ is an output signal from the emission detector for the calibration solution; and $I_R^{CALIBR}$ is an output signal from the reference detector for the calibration solution.

As discussed above with reference to FIG. 4, the controller 402 within the handheld fluorometer can calculate the concentration of the product in a sample based on the intensity signal from the emission detector. In some embodiments the controller 402 may also calculate the product concentration based on a calibration constant, zero shift, and/or an excitation reference signal using the relationships described above. Operation instructions for the controller may be stored in an onboard or discrete memory. In that respect, the memory may be a computer-readable medium comprising program instructions that cause the controller to provide any of the functionality ascribed to them, and perform any of the methods described herein. The controller may also store the raw fluorescence data obtained by the emission and/or reference detector(s) and other pertinent data in the memory. The controller may also store any calculated fluorescence values and/or concentration data in the memory.

As discussed above, in some embodiments of the invention fluorescence measurements can be taken by a handheld fluorometer by manually lowering the sensor head into a water sample. For example, a user can grasp the controller module and temporarily dip the immersible sensor head into a liquid sample such that the sensor head is partially or completely immersed in the sample and the water sample occupies the analytical area near the sensor head windows. Turning now to FIGS. 9-12, in some embodiments a sample cup is provided to contain a water sample about the immersible sensor head. A small volume of water from about 5 ml to about 20 ml can be sufficient for taking measurements in some embodiments.

Such handheld fluorometers are thus extremely portable, being able to measure fluorescence and determine the concentrations of products in a water flow while being removed from the source of the water sample. For example, the handheld fluorometer can be used to measure fluorescent emissions in the field or in a laboratory environment.

Embodiments of the invention are thus useful in many applications similar to those targeted by traditional cell-based fluorometers (e.g., in which a water sample is placed within an optically transparent cell). Embodiments of the invention, however, provide a number of advantages over cell-based fluorometers. For example, the sensor head of the handheld fluorometer described herein can be immersed within the water sample, while cell-based fluorometers rely on instrumentation located exterior to the cell to measure properties of the water within the cell. Accordingly, the handheld fluorometers herein avoid drawbacks associated with an optical cell such as signal degradation due to scratching or fouling of the cell surface. Similarly, minimal cleaning of the small area of the light source and emission detector windows can be contrasted with the time consuming cleaning or replacement usually required for optical cells. In addition, embodiments of the invention provide enhanced sensitivity due in part to the immediate proximity of the water sample to the light source/emission detector windows, which dramatically decreases the travel distance between the light source/emission detector and the product within the water sample. Accordingly, the heightened sensitivity provided in embodiments of the invention is useful for measuring very low concentrations of product (e.g., parts per million, ppm) and/or for measuring concentrations of product within a water sample having high color and/or turbidity.

Figure 9A:
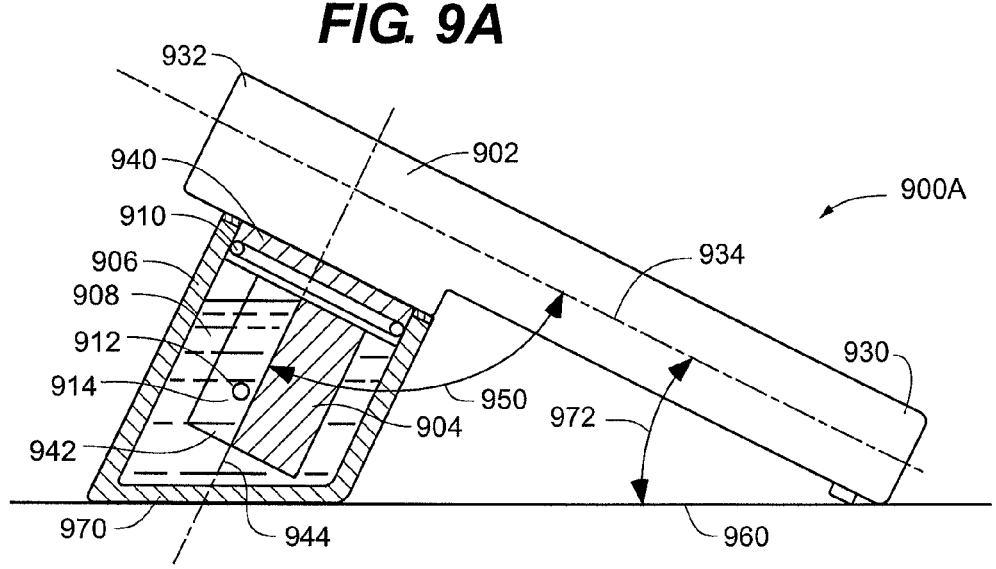
FIGS. 9A-9B are views showing a side view of a handheld fluorometer controller module and a cross-sectional view of a sample cup according to some embodiments of the invention.

FIG. 9A is a side view of a handheld fluorometer 900A having a controller module 902 connected with an immersible sensor head 904 according to some embodiments of the invention. The fluorometer 900A is also provided with a removable sample cup 906 adapted to contain a water sample 908 about the immersible sensor head 904. The sample cup 906 is removably coupled or fastened about the sensor head 904 with a fastener (not shown in FIGS. 9A-9B). In some embodiments the sample cup 906 is completely separable from the controller module 902 and the sensor head 904, which allows a user to easily remove the cup from the fluorometer for acquiring a water sample. For example, a user can unfasten and remove the sample cup, and then pour a water sample into the cup or use the cup to scoop a water sample from a larger reservoir or container. In some embodiments air escapes the sample cup as the sample cup is fastened about the sensor head and the sensor head 904 displaces air and water within the sample cup. This helps reduce or eliminate pockets of air that can be trapped within the sample cup and affect fluorescence measurements. In some cases an O-ring 910 or other sealing mechanism can help contain the water sample within the sample cup 906 when the sample cup 906 is fully attached about the sensor head 904. In some embodiments, though, the sample cup 906 may not be sealed about the sensor head 904 to allow further air to escape from the sample cup.

After acquiring a water sample 908 of adequate volume, the user fastens the sample cup 906 about the sensor head 904 and can begin the measurement process. Assuming that the water sample 908 is of sufficient volume (e.g., the cup was filled entirely), the light source window 912 and the emission detector window (not shown in FIG. 9A) will be immersed in the water sample 908 and the water sample 908 will occupy the analytical area 914 near the light source and emission detector windows, allowing the fluorometer 900A to determine a concentration of one or more products in the water sample 908. After measurements are completed, the water sample 908 can be discarded and the sample cup 906 refastened about the sensor head 904. Accordingly, the sample cup 906 can also provide a protective enclosure for the sensor head 904 when the fluorometer 900A is not in use. In some embodiments the sample cup 906 is made from a rigid plastic, which provides a durable and sturdy protective shell or cover for the sensor head 904. For example, in some cases the sample cup 906 may be composed of a polycarbonate, a PVC, or a polypropylene. In some embodiments, the sample cup 906 is composed of a clear polycarbonate, a grey PVC, or a black polypropylene. Other materials known in the art and having similar properties are also contemplated.

With continued reference to FIG. 9A, in some embodiments the sensor head 904 includes a housing having a proximal end 940 and a distal end 942, between which extends a length and longitudinal axis 944 of the sensor head 904. As described earlier herein, in some cases the sensor head 904 is connected (e.g., fastened or integrally formed) to a bottom surface of the controller module 902. The controller module 902 includes an elongated housing having a proximal end 930 and a distal end 932, between which extends a length of the controller module and a longitudinal axis 934 of the controller module 902. As shown in FIG. 9A, in some embodiments the sensor head 904 is connected to the bottom surface of the controller module housing proximate to the distal end 932 of the controller module housing. This configuration can provide a convenient form for a user to easily grasp the fluorometer 900A by the hand. Of course, other configurations for the controller module and sensor head are also possible, and the invention is not limited to any particular configuration.

In some embodiments the sample cup 906 and the controller module combine to form a substantially stable base for the fluorometer 900A upon a support surface 960. Referring to FIG. 9A, for example, a bottom portion 970 of the sample cup 906 can provide a first footing upon the support surface 960 and the proximal end 930 of the controller module 902 can provide a second footing. In some cases the geometry of the sample cup 906 and/or the proximal end 930 of the controller module may be configured to provide a substantially flat footing. For example, a bottom corner of the proximal end 930 of the controller module may be angled, while the bottom portion 970 of the sample cup 906 may also be angled.

It should be appreciated that the geometry of the sample cup 906 and the controller module 902 can be varied to provide a number of stationary configurations and/or orientations for the fluorometer 900A upon the support surface 960. For example, in some embodiments the longitudinal axis 934 of the controller module is angled with respect to the support surface 960 in a stationary position. The angle 972 of orientation with respect to the support surface 960 can in some embodiments provide a convenient viewing angle of the controller display when the fluorometer 900A is resting upon the support surface 960. The angle 972 can also advantageously accommodate the height of the sensor head above the support surface 960, while also providing a substantially stable base without the need for additional structure coupled to the controller module. In some cases the angle 972 may be between about 0 degrees and about 45 degrees. In some embodiments the angle 972 may be between about 10 and about 30 degrees. In some embodiments the angle 972 may be between about 25 and about 35 degrees. In some embodiments the angle 972 may be about 30 degrees. It should be appreciated that other angles are also possible.

In some embodiments of the invention, the orientation of the attachment between the sensor head 904 and the controller module 902 can be set to provide the fluorometer 900A with a desired inclined position on the support surface 960. For example, with reference to FIG. 9A, the sensor head 904 is connected to the controller module 902 such that the longitudinal axis 944 of the sensor head 904 forms a first angle 950 with the longitudinal axis 934 of the controller module. In some embodiments the angle 950 may range between about 60 degrees and about 90 degrees. As shown in FIG. 9A, the angle 950 is about 90 degrees.

Figure 9B:
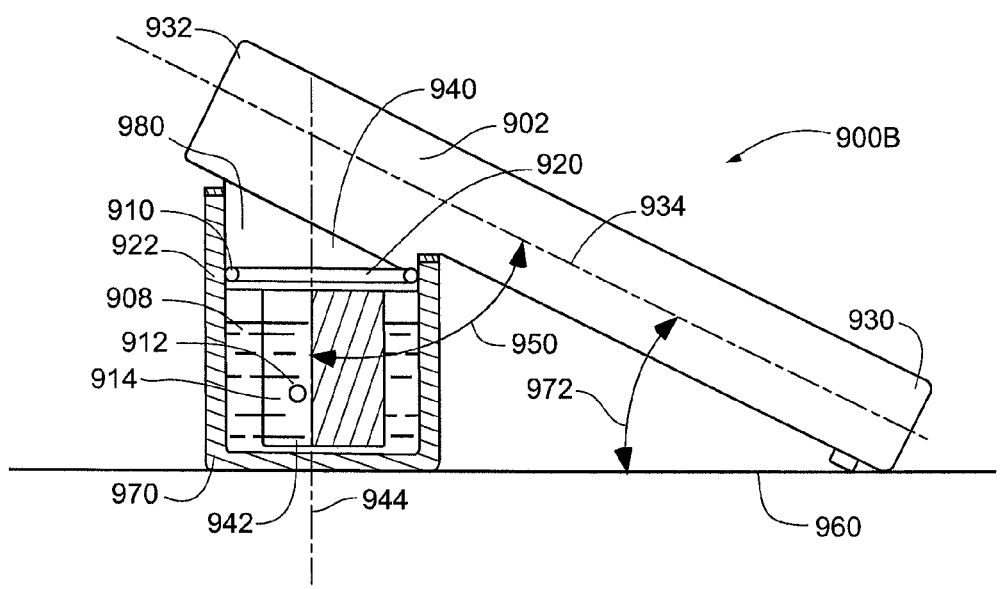

Turning to FIG. 9B, a fluorometer 900B is shown with many of the same components as shown in FIG. 9A. In this example, the controller module 902 is elevated above the support surface 960 at an angle 972 by coupling the sensor head 920 to the controller module 902 at a different angle 950 than that shown in FIG. 9A. For example, in some cases, the angle 950 shown in FIG. 9B may be about 60 degrees. As seen in FIG. 9B, in this embodiment the attachment angle provides the sensor head 920 in an upright position with its longitudinal axis substantially perpendicular to the support surface 960. An angled extension member 980 provides an angled interface between the sensor head 920 and the controller module 902. The sample cup 922 may be configured to specifically accommodate any orientation of the sensor head and the controller module. As shown in FIG. 9B, the sample cup 922 includes a relatively flat bottom portion 970 while including a somewhat angled top portion.

With reference now to both FIGS. 9A and 9B, in some embodiments of the invention one or more design parameters of the fluorometer are selected to maximize the likelihood that the water sample 908 will occupy the analytical area 914 and minimize the likelihood that air within the sample cup will occupy the analytical area, adversely impacting measurements. For example, as previously mentioned, the sample cup may not be tightly sealed about the sensor head in some embodiments in order to allow air to escape the sample cup as the sensor head is lowered into the cup. In some embodiments, the sensor head is configured with one or more angled exterior surfaces to urge potentially trapped air bubbles toward the surface of the water sample. For example, the sensor head 904 in FIG. 9A presents an angled end surface at the distal end 942 of the sensor head, which minimizes locations where air bubbles may become trapped. In addition, in some embodiments the light source window and the emission detector window are positioned near the distal end 942 of the sensor head in order to locate them farther away from the surface of the water sample and make it further unlikely that the light source window and the emission detector window will be exposed to air during operation.

Figure 10:
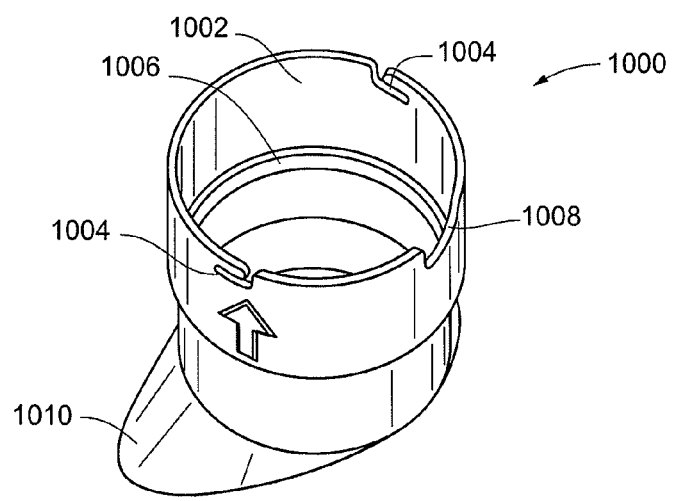
FIG. 10 is a top perspective view of a sample cup according to some embodiments of the invention.

FIG. 10 is a top perspective view of a sample cup 1000 according to some embodiments of the invention. The sample cup 1000 generally includes a cylindrical wall 1002 and a bottom wall forming a receptacle for containing a water sample about the sensor head of a fluorometer. In some embodiments the sample cup 1000 also includes a support pad 1010 attached to or integral with the bottom and/or cylindrical wall for stabilizing the support cup and fluorometer upon a support surface. The sample cup further includes a portion of a fastener in the form of L-shaped bayonet slots 1004. Corresponding pins on the sensor head or controller module of a fluorometer can engage the slots 1004 to removably fasten the sample cup 1000 about the sensor head of the fluorometer. In some embodiments, the sample cup 1000 includes a suggested water level mark or relief 1006, which can indicate a preferred volume of water to be included by a user.

In some embodiments, an overfill outlet or opening 1008 provides a path out of the sample cup 1000 for excess sample water when the sensor head is inserted into the sample cup 1000. The overfill outlet 1008 may be a modified (e.g., enlarged) fastener slot in or near the rim of the sample cup, similar to the bayonet slots 1004 in some embodiments. In some cases the overfill outlet is provided in the sensor head housing or the controller module housing rather than, or in addition to, the sensor cup. In some embodiments the overfill outlet 1008 is advantageously located out of line of sight of the analytical area and the emission detector window in the sensor head to minimize any potential effect on measurements from stray light entering the sample cup 1000 through the overfill opening 1008.

In some embodiments the sample cup 1000 comprises a material that is opaque to the light wavelengths to which the emissions detector is sensitive. In some embodiments, the sample cup material is opaque to the light wavelengths generated by the fluorometer light source to reduce the chance that any ambient or stray light may enter the analytical area and trigger fluorescence apart from the light source. As just one example, in some embodiments the sample cup 1000 may be opaque to UV radiation within a range from about 280 nm to about 320 nm and within in a range from about 300 nm to about 420 nm useful for embodiments of the fluorometer described above. In some embodiments a clear polycarbonate can be used to provide protection from ambient light and allow visual control of the water sample level.

Figure 11:
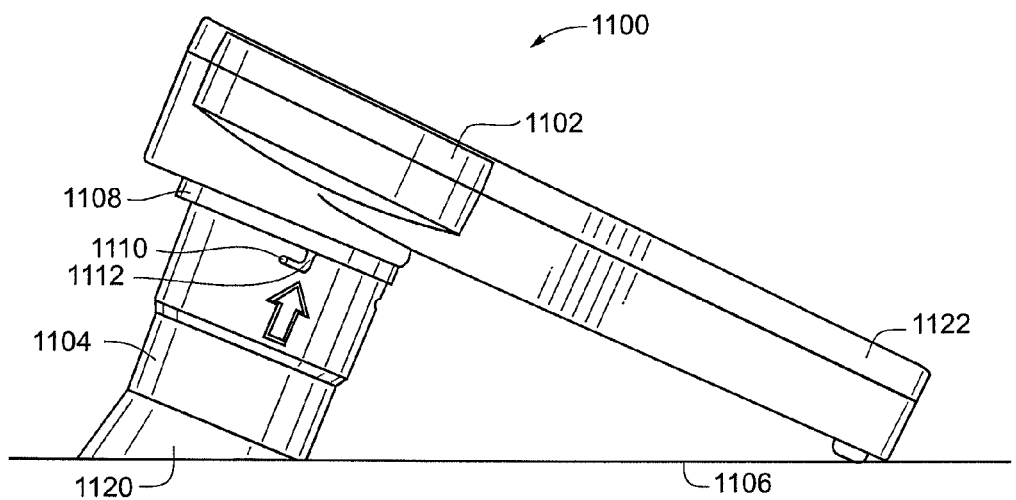
FIG. 11 is a side view of a handheld fluorometer according to some embodiments of the invention.

FIG. 11 is a side view of a handheld fluorometer 1100 according to some embodiments of the invention. The fluorometer 1100 includes a sample cup 1104 attached about the sensor head 1108 using a fastener comprising bayonet slots 1112 and pins 1110. Those skilled in the art will appreciate that a wide variety of fasteners in addition to bayonet slots/pins are possible. For example, the fastener may include various other configurations of pins and slots, screw threads, snapping elements, pressure locking elements, magnets incorporated into the cup and sensor head/controller module and/or other fasteners. In some embodiments the fastener may include nothing more than a light pressure fit between the inner wall of the sample cup 1104 and a mating surface on the sensor head 1108 or controller module 1102. According to some embodiments, the fastener is configured to align the sample cup 1104 in a preferred orientation with respect to the sensor head 1108 and/or the controller module 1102. For example, the bayonet slots 1112 and pins 1110 shown in FIG. 11 can align the sample cup 1104 with the support pad 1120 in a preferred rotation with respect to the controller module and the support surface 1106 to provide a substantially stable base.

Figure 12:
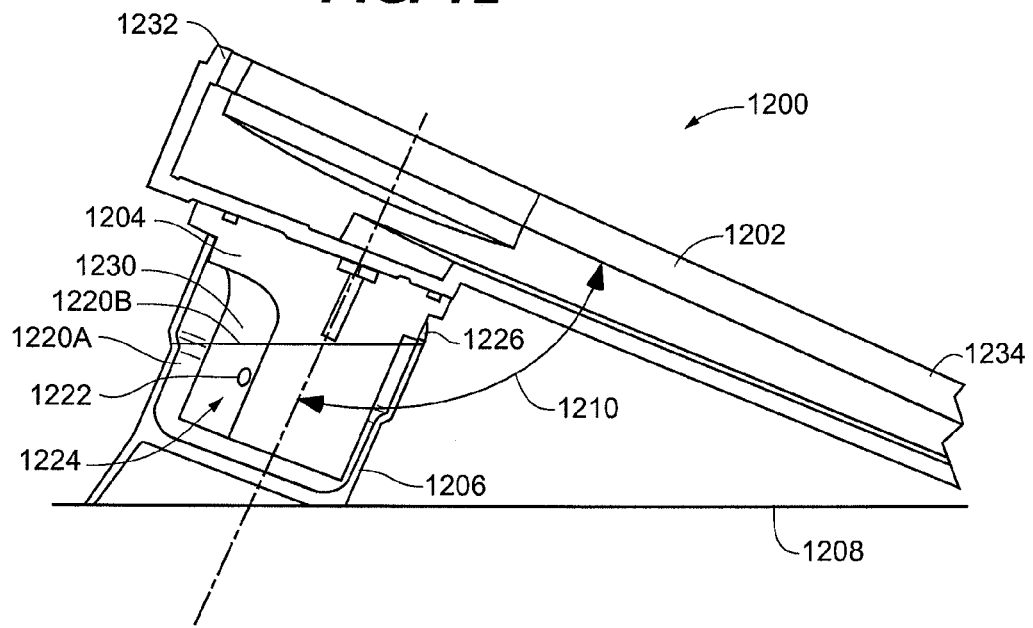
FIG. 12 is a side view of a handheld fluorometer including a cross-sectional view of a sample cup and sensor head according to some embodiments of the invention.

FIG. 12 is a side view of a handheld fluorometer 1200 having a controller module 1201 and a cross-sectional view of a sample cup 1206 according to some embodiments of the invention. The fluorometer 1200 includes a controller module 1202 connected to a sensor head 1204 in a similar manner to FIG. 11. The sensor head 1204 is partially immersed in the water sample 1220A, creating a typical water level 1220B within the sample cup 1206 according to some embodiments of the invention. The emission detector window 1222 and the light source window (not shown) are immersed below the water surface 1220B such that the water sample 1220A occupies the analytical area 1224 next to the emission detector window 1222. In some embodiments the overfill outlet 1226 is advantageously located out of line of sight of the analytical area 1224 and the emission detector window 1222 to minimize any potential effect from stray light entering the sample cup 1206 through the overfill opening 1226. In some cases the overfill opening 1226 is located in the sample cup (e.g., as shown in FIG. 10). In some cases, the overfill outlet may be provided in the sensor head housing or the controller module housing rather than, or in addition to, the sensor cup.

As discussed above herein, in some embodiments one or more design parameters of the fluorometer can be set to maximize the likelihood that the emission detector 1222 and the light source will be immersed below the surface 1220B of the water sample and that the water sample 1220A will occupy the analytical area 1224 when the fluorometer 1200 is set in a stationary position upon a support surface 1208. For example, in some cases the angle 1210 between the sensor head 1204 and the controller module 1202, the location and size of the overfill outlet 1226, the shape of the cutout 1230 in the sensor head 1204, the position of the light source and emission detector windows within the sensor head, and/or the shape of the sample cup 1206 are set with the expectation that, given an adequate volume of the water sample 1220A, the water sample will occupy the analytical area 1224 when the fluorometer 1200 is positioned upon the support surface 1208.

As shown in FIG. 12, the angular cutout 1230, including the light source window (not shown) and the emission detector window 1222, are oriented with respect to the controller module such that the angular cutout and the windows face toward the distal end 1232 of the controller module 1202. In some embodiments the angular cutout and the windows may be oriented in a different direction with respect to the controller module 1202. As just one example, in some embodiments the sensor head 1204 is connected to the controller module 1202 such that the angular cutout 1230 and the windows face toward the proximal end 1234 of the controller module 1202.

Figure 13:
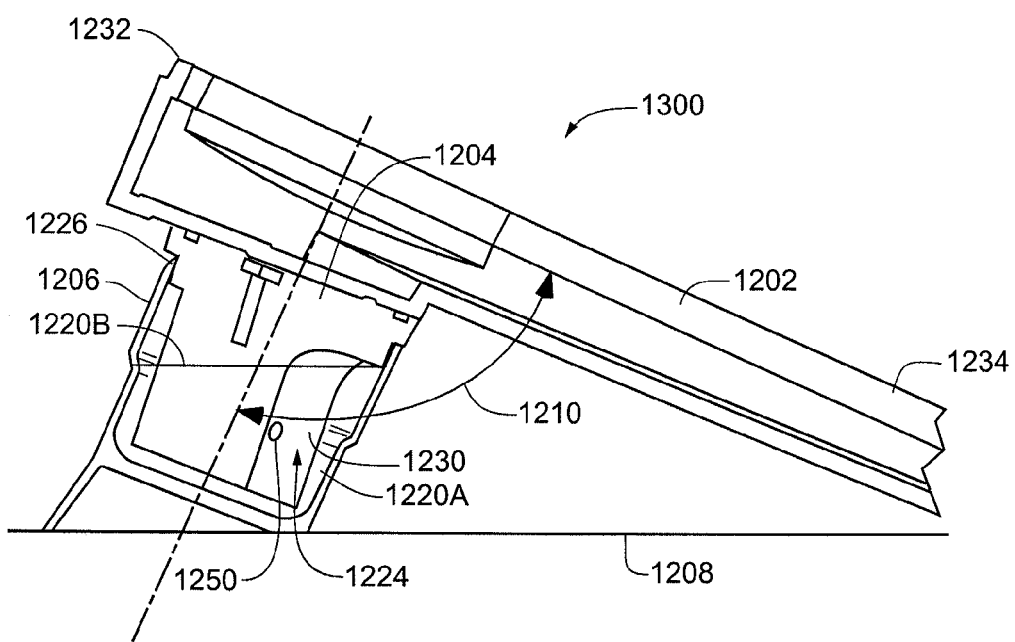
FIG. 13 is a side view of a handheld fluorometer including a cross-sectional view of a sample cup and sensor head according to some embodiments of the invention.

Various rotational orientations of the sensor head 1204 can also provide a number of benefits depending upon the tilt of the sensor head 1204 with respect to the support surface 1208 and the water sample surface 1220B. For example, some rotational orientations may provide a potentially deeper location for the emission detector window within the sample cup 1206, thus increasing the likelihood that the water sample will occupy the analytical area. As shown in FIG. 13 for example, in some embodiments the sensor head 1204 is rotated so that the cutout 1230 faces the proximal end 1234 of the controller module and the emission detector or light source window 1250 is positioned further from the surface 1220B of the water sample. In some cases it has also been noted that reflections off the surface 1220B of the water sample 1220A can interfere with fluorescence measurements. In some embodiments the rotation of the sensor head 1204 can be set to minimize the effect of the such reflections. As just one example, the cutout 1230 and sensor head windows may be oriented in the direction of the proximal end 1234 of the controller module as in FIG. 13 to minimize such reflections.

In cases where the sensor head 1204 is rotated so that the cutout 1230 faces the proximal end 1234 of the controller module, the overfill outlet 1226 can still be advantageously located out of line of sight of the analytical area 1224. For example, as shown in FIG. 13 the overfill outlet 1226 may be positioned in the opposite side of the sample cup 1206, near the distal end 1232 of the controller module. Thus, the positioning can minimize any potential effect from stray light entering the sample cup 1206 through the overfill opening 1226. In some cases the overfill opening 1226 is located in the sample cup as illustrated. In some cases, the overfill outlet may be provided in the sensor head housing or the controller module housing rather than, or in addition to, the sensor cup.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A handheld fluorometer, comprising:
a handheld controller module comprising
an elongated housing comprising a bottom surface,
a controller that determines a concentration of a substance in a water sample based on a detected fluorescent emission,
a display coupled to the controller for displaying the concentration, and
an input interface for entering data for use by the controller;
an immersible sensor head comprising
a light source coupled to the controller,
an emission detector coupled to the controller, and
a housing comprising a proximal end and a distal end between which extends a longitudinal axis of the sensor head, the sensor head being connected to the bottom surface of the controller module at the proximal end of the sensor head housing,
the sensor head housing further comprising a light source window that transmits excitation light from the light source inside the sensor head housing to an analytical area outside the sensor head housing, and an emission detector window that transmits fluorescent emissions from the analytical area to the emission detector inside the sensor head housing;
a sample cup for containing the water sample; and
a fastener that removably fastens the sample cup about the sensor head such that at least the light source window and the emission detector window can be immersed in the water sample contained in the sample cup, wherein the water sample occupies the analytical area.

2. The handheld fluorometer of claim 1, wherein the controller module housing further comprises a first end and a second end between which extends a longitudinal axis of the controller module housing, and wherein the sensor head is connected to the bottom surface of the controller module such that the longitudinal axis of the sensor head and the longitudinal axis of the controller module housing form a first angle of between about 60 degrees and about 90 degrees.

3. The handheld fluorometer of claim 2, wherein the first angle is about 90 degrees.

4. The handheld fluorometer of claim 2, wherein the first angle is about 60 degrees.

5. The handheld fluorometer of claim 2, wherein the sensor head is positioned proximate to the first end of the controller module housing, and wherein the second end of the controller module housing and the sample cup provide a substantially stable base for the handheld fluorometer in a stationary position upon a support surface.

6. The handheld fluorometer of claim 5, wherein the longitudinal axis of the controller module housing is angled with respect to the support surface in the stationary position.

7. The handheld fluorometer of claim 1, wherein the sample cup comprises an overfill opening that provides a path out of the sample cup for excess sample water when the sensor head is positioned within the sample cup.

8. The handheld fluorometer of claim 7, wherein the overfill opening is positioned out of line of sight of the emission detector window with the sample cup fastened about the sensor head.

9. The handheld fluorometer of claim 8, wherein the fastener aligns the sample cup with respect to the sensor head.

10. The handheld fluorometer of claim 1, wherein the fastener comprises one or more pins and one or more corresponding slots.

11. The handheld fluorometer of claim 1, wherein the light source emits light in a first UV wavelength range and the emission detector detects emissions within a second UV wavelength range.

12. The handheld fluorometer of claim 11, wherein the sample cup comprises a material opaque to the first and the second UV wavelength ranges.

13. A handheld fluorometer, comprising:
a handheld controller module comprising
an elongated housing comprising a bottom surface and a first end and a second end between which extends a longitudinal axis of the housing,
the controller module further comprising a controller that determines a concentration of a substance in a water sample based on a detected fluorescent emission, and
a display coupled to the controller for displaying the concentration;
an immersible sensor head comprising
a UV light source coupled to the controller,
a UV emission detector coupled to the controller, and
a housing comprising a proximal end and a distal end between which extends a longitudinal axis of the sensor head, the sensor head being connected to the bottom surface of the controller module housing at the proximal end of the sensor head housing such that the longitudinal axis of the sensor head is approximately perpendicular to the longitudinal axis of the controller module housing,
the sensor head housing further comprising a light source window that transmits UV excitation light from the UV light source inside the sensor head housing to an analytical area outside the sensor head housing, and an emission detector window that transmits UV fluorescent emissions from the analytical area to the UV emission detector inside the sensor head housing; and
at least a first portion of a fastener configured to removably fasten a sample cup about the sensor head.

14. The handheld fluorometer of claim 13, wherein the sensor head housing is fixedly attached to the bottom surface of the controller module housing at the proximal end of the sensor head housing.

15. The handheld fluorometer of claim 13, wherein the sensor head housing is integrally connected to the bottom surface of the controller module housing at the proximal end of the sensor head housing.

16. The handheld fluorometer of claim 13, further comprising a sample cup for containing the water sample, the sample cup comprising at least a second portion of the fastener configured to cooperate with the first portion of the fastener to removably fasten the sample cup about the sensor head such that at least the light source window and the emission detector window can be immersed in the water sample contained in the sample cup, wherein the water sample occupies the analytical area.

17. The handheld fluorometer of claim 16, wherein the first portion of the fastener comprises a fastening surface of the handheld fluorometer and the second portion of the fastener comprises a fastening surface of the sample cup, the fastening surfaces configured to engage one another in a press fit.

18. The handheld fluorometer of claim 16, wherein the first portion of the fastener comprises one or more pins and the second portion of the fastener comprises one or more corresponding slots.

19. A handheld fluorometer, comprising:
a handheld controller module comprising
an elongated housing comprising a bottom surface and a first end and a second end between which extends a longitudinal axis of the housing,
the controller module further comprising a controller that determines a concentration of a substance in a water sample based on a detected fluorescent emission, and
a display coupled to the controller for displaying the concentration;
an immersible sensor head comprising
a UV light source coupled to the controller,
a UV emission detector coupled to the controller, and
a housing comprising a proximal end and a distal end between which extends a longitudinal axis of the sensor head, the sensor head being connected to the bottom surface of the controller module housing at the proximal end of the sensor head housing such that the longitudinal axis of the sensor head is approximately perpendicular to the longitudinal axis of the controller module housing,
the sensor head housing further comprising a light source window that transmits UV excitation light from the UV light source inside the sensor head housing to an analytical area outside the sensor head housing, and an emission detector window that transmits UV fluorescent emissions from the analytical area to the UV emission detector inside the sensor head housing; and
a sample cup for containing the water sample and a fastener that removably fastens the sample cup about the sensor head such that at least the light source window and the emission detector window can be immersed in the water sample contained in the sample cup, wherein the water sample occupies the analytical area.

20. The handheld fluorometer of claim 19, wherein the sample cup comprises an overfill opening that provides a path out of the sample cup for excess sample water when the sensor head is positioned within the sample cup.

21. A method for measuring fluorescent emissions from a substance and determining the concentration of the substance within a water sample, comprising:
providing a handheld fluorometer comprising a handheld controller module, an immersible sensor head connected to a bottom surface of the controller module at a proximal end of the sensor head, and at least a first portion of a fastener configured to removably fasten a sample cup about the sensor head;
immersing the sensor head in a water sample containing a concentration of a substance;
generating and directing UV excitation light into the water sample, whereby the substance fluoresces when contacted by the UV excitation light;
detecting UV fluorescent emissions from the water sample with the handheld fluorometer; and
determining the concentration of the substance in the water sample with the handheld fluorometer based on the detected UV fluorescent emissions.

22. The method of claim 21, wherein immersing the sensor head in the water sample comprises temporarily lowering and suspending the handheld fluorometer by hand above a water sample such that at least a portion of the sensor head is immersed in the water sample.

23. The method of claim 21, wherein immersing the sensor head in the water sample comprises:
providing a sample cup comprising at least a second portion of the fastener configured to cooperate with the first portion of the fastener;
filling the sample cup with the water sample; and
fastening the sample cup to the handheld fluorometer about the sensor head such that at least a portion of the sensor head is immersed in the water sample.

24. A method for measuring fluorescent emissions from a substance and determining the concentration of the substance within a water sample, comprising:
providing a handheld fluorometer comprising a handheld controller module and an immersible sensor head connected to a bottom surface of the controller module at a proximal end of the sensor head;
immersing the sensor head in a water sample containing a concentration of a substance;
generating and directing UV excitation light into the water sample, whereby the substance fluoresces when contacted by the UV excitation light
detecting UV fluorescent emissions from the water sample with the handheld fluorometer; and
determining the concentration of the substance in the water sample with the handheld fluorometer based on the detected UV fluorescent emissions;
wherein immersing the sensor head in the water sample comprises:
providing a sample cup;
filling the sample cup with the water sample; and
fastening the sample cup to the handheld fluorometer about the sensor head such that at least a portion of the sensor head is immersed in the water sample.

* * * * *